United States Patent [19]

Ryang

[11] 4,381,396

[45] Apr. 26, 1983

[54] SILYNORBORNANE ANHYDRIDES AND METHOD FOR MAKING

[75] Inventor: Hong-Son Ryang, Schenectady, N.Y.

[73] Assignee: General Electric Company, Schenectady, N.Y.

[21] Appl. No.: 395,932

[22] Filed: Jul. 7, 1982

[51] Int. Cl.$^3$ .................. C07D 307/89; C07D 307/93
[52] U.S. Cl. ................................. 549/237; 549/234; 549/235; 549/236
[58] Field of Search ................ 549/234, 235, 236, 237

[56] References Cited

U.S. PATENT DOCUMENTS

| | | | |
|---|---|---|---|
| 3,105,087 | 9/1963 | Roberts et al. ................. | 549/235 X |
| 3,288,754 | 11/1966 | Green ................................ | 260/47 |
| 3,325,450 | 6/1967 | Holub ............................... | 260/46.5 |
| 3,338,859 | 8/1967 | Green ................................ | 260/30.2 |
| 3,476,546 | 11/1969 | Roberts et al. ................. | 549/237 X |
| 4,254,044 | 3/1981 | Sprague .......................... | 549/237 X |

OTHER PUBLICATIONS

Siloxanmodifizierte Polypyromellitimide, Kuckertz, Die Makromolekulare Chemie, 98, (1966), 101–108.
Polyimides from Silicon-Containing Dianhydrides and Diamines, Johnston et al., ACS Org. Cont. Plast. Chem., V. 33, 1973, pp. 169–176.
Organosilicon Compounds, XVIII, Silicon-Containing Dianhydrides, Pratt et al., J. Org. Chem., vol. 38, No. 25, 1973, pp. 4271–4274.
Effect of Elastomer Chain Length on Silicone-Modified Polyimide Properties, Ezzell et al., Abstract of 33rd Southern Regional ACS Mtg., p. 107, (1981).
Moshinskii et al., Chemical Abstracts, vol. 72, (1970).
Derwent, Week D38, p. 17, Soviet Union 761,521, 4/9/78.
Nishizaki et al., Chem. Abstracts, vol. 63, 1965, 3057b.

*Primary Examiner*—Paul F. Shaver
*Attorney, Agent, or Firm*—William A. Teoli; James C. Davis, Jr.; James Magee, Jr.

[57] ABSTRACT

Silylnorbornane anhydrides are provided by effecting reaction between a silicon hydride and a norbornene carboxylic acid anhydride in the presence of a platinum catalyst. The resulting silicon functionalized norbornane monoanhydrides or dianhydrides can be used to synthesize a variety of tough organosilicon polyimide copolymers and polydiorganosiloxane polyimide block polymers.

18 Claims, No Drawings

SILYNORBORNANE ANHYDRIDES AND METHOD FOR MAKING

CROSS REFERENCE TO RELATED APPLICATIONS

References is made to my copending application RD-14212, for Silicone-Imide Copolymers and Method for Making, filed concurrently herewith and assigned to the same assignee as the present invention.

BACKGROUND OF THE INVENTION

The present invention is directed to silylnorbornane anhydrides and method for making. More particularly, the present invention relates to the hydrosilation of norbornene carboxylic acid anhydride with a silicon hydride in the form of a silane, disiloxane, or polysiloxane.

Prior to the present invention, indirect methods were available for synthesizing silicon functional anhydrides involving the addition of silanes to ortho alkyl substituted aromatic hydrocarbon followed by oxidation of the alkyl groups as shown by J. R. Pratt et al, J. Org. Chem., 38 4271 (1973). Another procedure involved the reaction of maleic anhydride with cyclopentadiene attached by carbon-silicon linkages onto a polysiloxane backbone to produce a siloxane functionalized by 5-norbornene-2,3-carboxylic anhydride groups as shown by L. Ya. Moshinskii et al, U.S.S.R. No. 244616 (1969) [Chem. Abstracts 72, 32777m (1970)].

Direct reaction of unsaturated anhydrides, for example, allyl succinic anhydride with trichlorosilane is reported by Walter Hafner et al, Chem. Abstracts, 212163J, Vol. 91, page 24 (1979). Attempts to directly react silicon hydride with cyclic anhydride having internal aliphatic unsaturation, for example, maleic anhydride and tetrahydrophthalic anhydride to produce silyl anhydrides have been unsuccessful. The reason why direct hydrosilation has been found successful with aliphatically unsaturated cyclic anhydrides having the aliphatic unsaturation in a side chain such as allylsuccinic anhydride rather than internal ring unsaturation, such as maleic anhydride, is not completely understood. One possible explanation is that terminal olefins are much more reactive than internal olefins.

The present invention is based on the discovery that although cyclic anhydrides having internal aliphatic unsaturation normally do not react with silicon hydride, 5-norbornene-2,3-carboxylic anhydride of the formula,

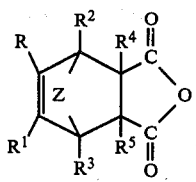
(1)

where R-R$^5$ are a members selected from hydrogen, halogen, C$_{(1-13)}$ monovalent hydrocarbon radicals and substituted C$_{(1-13)}$ monovalent hydrocarbon radicals, Z is selected from —O— and C—(R)$_2$, readily reacts with silicon hydride in the presence of a platinum catalyst to produce silyl norbornane anhydrides or dianhydrides.

STATEMENT OF THE INVENTION

There is provided by the present invention, silylnorbornane anhydrides of the formula

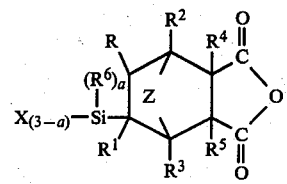
(2)

where R-R$^5$ and Z are as previously defined, R$^6$ is selected from C$_{(1-13)}$ monovalent hydrocarbon radicals and substituted monovalent hydrocarbon radicals, and X is a member selected from the class consisting of, (a) a hydrolyzable radical selected from the class consisting of halo, hydrogen, C$_{(1-8)}$ alkoxy, acyloxy, —N(R$^7$)$_2$, cyano, amido, carbamato, enoxy, imidato, isocyanato, oximato, isocyanate, oximato, thioisocyanato and ureido, (b) siloxanes having the formula,

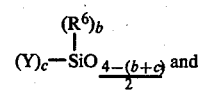 and (c) polysiloxanes having the formula,

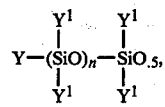

where R$^6$ is as previously defined, R$^7$ is selected from monovalent hydrocarbon radicals, Y is selected from a radical having the formula,

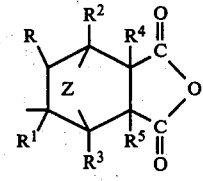

and (a) radicals, Y$^1$ is selected from R$^6$ radicals, Y radicals and mixtures thereof, a is a whole number equal to 0 to 3 inclusive, b is a whole number equal to 0 to 3 inclusive, c is a whole number equal to 0 to 3 inclusive, the sum of b+c is equal to 0 to 3 inclusive and n is an integer equal to 1 to 2000 inclusive.

Radicals included within R-R$^5$, are for example, halogen such as chloro, bromo, etc. Among R-R$^6$ radicals there are included, aryl radicals and halogenated aryl radicals, for example, phenyl, chlorophenyl, tolyl, xylyl, biphenyl, naphthyl, etc.; alkenyl radicals, for example, vinyl, allyl, cyclohexenyl, etc.; C$_{(1-8)}$ alkyl radicals, halogenated alkyl and aminoalkyl radicals, for example, methyl, ethyl, propyl, butyl, octyl, etc. R$^7$ is selected from C$_{(1-8)}$ alkyl radicals, for example, methyl, ethyl, propyl, etc., and C$_{(6-13)}$ aryl radicals, for example, phenyl, tolyl, etc. In instances where R-R$^7$ is more than one radical, these radicals can be all the same or any two or more the aforementioned radicals.

Silylnorbornane anhydrides included within formula (2) are, for example,

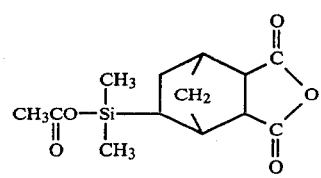
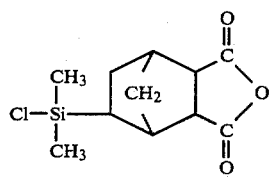
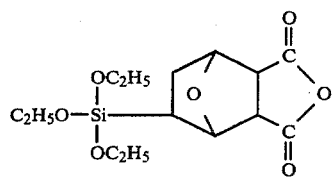
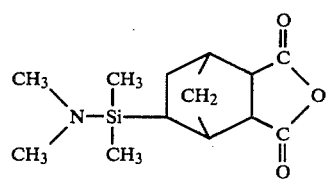
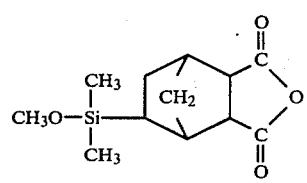
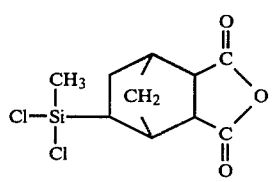
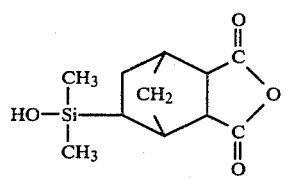
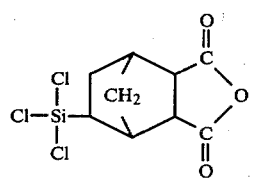

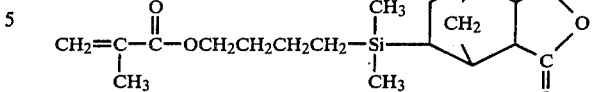

Siloxane norbornane anhydrides included within formula (2) are, for example,

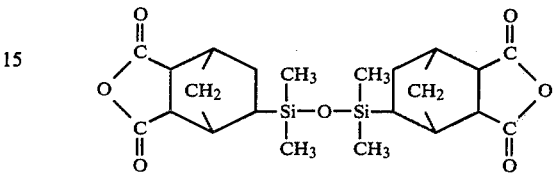

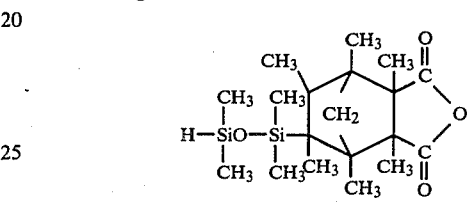

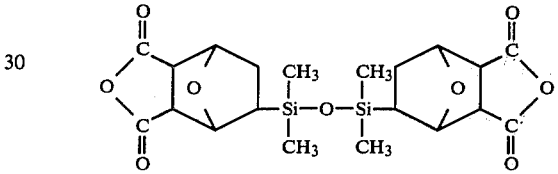

Polysiloxane norbornane anhydrides included within formula (2) are, for example,

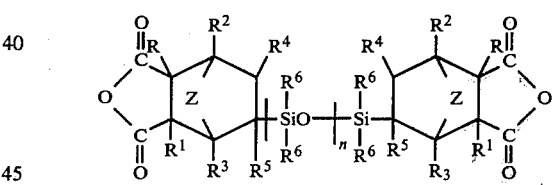

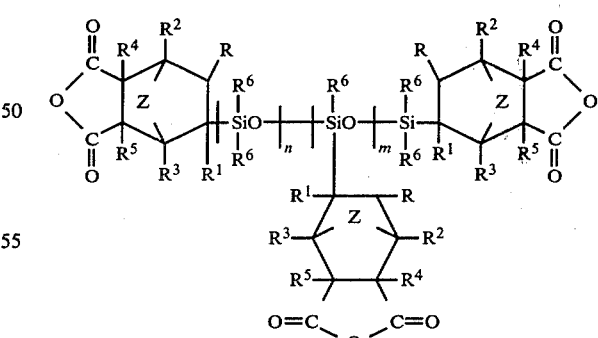

where $R$-$R^6$, Z and n are as previously defined, m is an integer equal to 0 to 500 inclusive and the sum of m+n is equal to 1 to 2000 inclusive.

In another aspect of the present invention there is provided a method for making silylnorbornane anhydrides included within formula (2) which comprises effecting reaction between a norbornene anhydride of formula (1) with a silane of the formula,

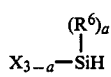

in the presence of an effective amount of a platinum catalyst, where X, $R^6$ and a are as previously defined.

Experience has shown that the hydrosilation reaction between the norbornene anhydride of formula (1) and the silane of formula (3) can be facilitated in the presence of an inert organic solvent, for example, diglyme, toluene, chlorobenzene, ethylene glycoldimethylether, tetrahydrofuran, etc. In instances where monohydrosilation isomers are formed, longer reaction times and high temperatures, for example, temperatures exceeding 100° C. may be required for dianhydride formation.

If an increase is desired in the molecular weight of organopolysiloxane having chemically combined norbornane anhydride siloxy units attached to silicon by carbon-silicon linkages, the lower molecular weight norbornane substituted siloxane can be equilibrated with a cyclic siloxane, for example octa-methylcyclotetrasiloxane in the presence of an acid catalyst such as sulfuric acid. A typical reaction is as follows:

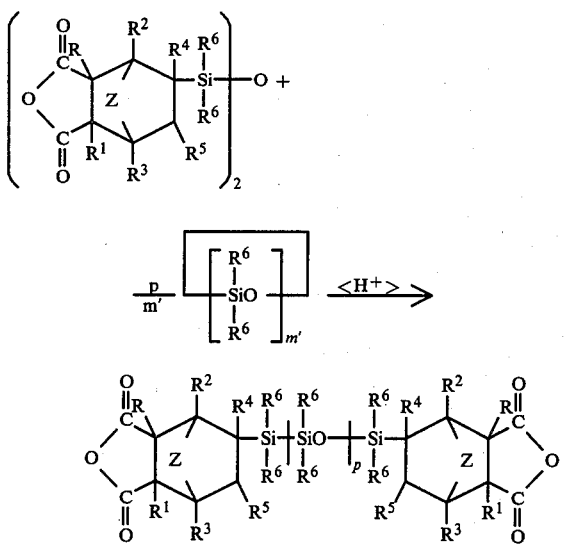

where $R^6$ and Z are as previously defined, p is a positive integer and m' has a value of 3 to 6 inclusive.

Hydrosilation catalysts which can be used in the practice of the present invention are, for example, unsaturated siloxanes, as shown by Karstedt U.S. Pat. No. 3,775,442, Ashby U.S. Pat. Nos. 3,159,601, and 3,159,662 and Lamoreaux U.S. Pat. No. 3,220,972, assigned to the same assignee as the present invention. An effective amount of a platinum catalyst is about 0.001% to 0.1% by weight of platinum, based on the weight of the hydrosilation mixture or the intercondensation mixture.

The silylnorbornane anhydrides of formula (2) can be used as intermediates for making polyimidepolydiorganosiloxane block polymers based on the reaction of organic diamines, for example, meta-phenylene diamine, with bisanhydrides included within formula (1) and mixtures of such anhydrides with other bisanhydrides, for example, benzophenone dianhydride, pyromellitic dianhydride, and aromatic bis(ether anhydride)s as shown in my copending application RD-14212, filed concurrently herewith. Further, some of the silylnorbornane anhydrides included within formula (2) can be used as adhesion promoters for room temperature vulcanizable organopolysiloxane compositions.

In order that those skilled in the art will be better able to practice the invention, the following examples are given by way of illustration and not by way of limitation. All parts are by weight.

EXAMPLE 1

There was added 10 drops of a 5% platinum catalyst prepared in accordance with Karstedt, U.S. Pat. No. 3,775,442, assigned to the same assignee as the present invention, to a mixture while it was being stirred of 69.4 g (0.42 mole) of 5-norbornene-2,3-dicarboxylic acid anhydride, 26.8 g (0.2 mole) 1,1,3,3-tetramethyldisiloxane and 100 ml of dry chlorobenzene. The resulting mixture was heated with stirring to 70°-80° C. for 4 hours and then 100°-110° C. overnight. After cooling, carbon black was added and the solution was stirred for 30 minutes at room temperature. Filtration, removal of the solvent at 100° C. with a vacuum pump and addition of dry diethylether resulted in the precipitation of a white crystalline solid. Based on method of preparation, the product was 5,5'-(1,1,3,3-tetramethyl-1,3-disiloxanediyl)-bis-norbornane-2,3-dicarboxylic anhydride having the formula,

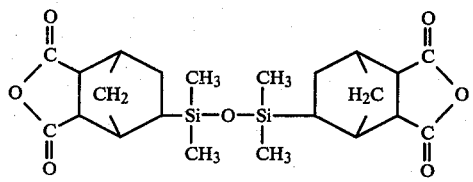

The identity of the above dianhydride was further confirmed by NMR, IR, Mass spectrometry and elemental analysis.

There was added a mixture of 0.57 grams of the above 5,5'-(1,1,3,3-tetramethyl-1,3-disiloxanediyl)-bis-norbornane-2,3-dicarboxylic anhydride, 1.289 grams benzophenone tetracarboxylic dianhydride and 5 ml of dimethylformamide to a solution of 0.991 gram of methylene dianiline and 5 ml of dimethylformamide while it was stirred under nitrogen. The resulting solution was stirred for 2 hours at room temperature. A part of the solution was poured into a glass dish and dried at 80° C. for 1 hour, then 150° C. for 2 hours in an oven under nitrogen. There was obtained a silicone polyimide copolymer having a Tg of 243° C. The copolymer is useful as high temperature insulation for metallic conductors.

EXAMPLE 2

There was added 10 drops of the platinum catalyst used in Example 1 under a nitrogen atmosphere to a mixture of 8.36 grams of 5-norbornene-2,3-dicarboxylic anhydride, 44.8 grams of an alpha,omega-dihydrogen polydimethylsiloxane having an average molecular weight of 1790 and 100 ml of chlorobenzene. The mixture was stirred and heated to 60°-80° C. overnight. After cooling, carbon black was added and the solution was stirred for 30 minutes at room temperature. A colorless viscous oil was obtained when the resulting mixture was filtered and solvent was removed at 100° C. in vacuo. Based on method of preparation, there was obtained a norbornane anhydride end-capped polydimethylsiloxane having the formula,

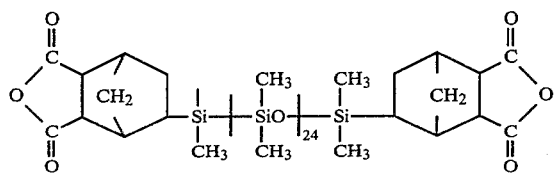

The identity of the above material was further confirmed by NMR analysis.

There was added a mixture of 0.53 grams of the above polysiloxane dianhydride and 0.725 grams of benzophenone dianhydride and 5 ml of dimethylformamide under nitrogen to a mixture of 0.496 grams of methylene dianiline and 5 ml of dimethylformamide while the mixture was stirred under nitrogen. The resulting solution was stirred for 2 hours at room temperature. The resulting solution was then poured into a glass dish and dried at 80° C. for 1 hour and then 150° C. for 2 hours in an oven under nitrogen. There was obtained a film having a Tg of 271° C. Based on method of preparation, the product was a block copolymer. The block copolymer is useful as a polyimide impact modifier.

EXAMPLE 3

A mixture of 5-norbornene-2,3-dicarboxylic anhydride (1.64 gm, $10^{-2}$ mole), dimethylchlorosilane (1.5 gm, $1.6 \times 10^{-2}$ mole), 5 drops of the catalyst of Example 1, and 30 ml of toluene was sealed under anhydrous conditions and heated to 60°–80° C. overnight. After removal of the volatile materials under vacuum, the residue was analyzed by NMR, IR and GC/Mass which confirmed the quantitative formation of 5-dimethylchlorosilylnorbornane-2,3-dicarboxylic anhydride: HNMR S(in CDCl₃, 7.25 ppm internal standard) 3.43 (2 H,m) 2.85 (2 H, m), 1.90~1.56 (4 H,m), 0.90 (1 H,t), 0.42(3 H,S), and 0.37 (3 H,S); IR (neat) 2960, 2870, 1850 and 1770 cm⁻¹. Mass (Intensity%) 260 (M+2, 1.4%), 258 (M+, 2.9), 192 (8.6), 159 (28.5), 95 (60.3), 93 (100), 66 (97.4). Without further purification, the product was subsequently mixed with H₂O (0.2 gm) at 0° C. in tetrahydrofuran (20 ml), and then stirred at room temperature for 2 hours. The volatile materials were removed and the residue was heated to 200° C. under vacuum for 2 hours. After addition of dry diethyl ether, the white precipitate (1.8 gm, 80% yield) was collected and dried. Spectroscopic data of the product were identical to those for 5,5'-(1,1,3,3-tetramethyl-1,1,3-disiloxanediyl)-bis-norbornane-2,3-dicarboxylic anhydride of Example 1.

EXAMPLE 4

There was added 1 drop of 96% sulfuric acid to a mixture of 2.75 g of the dianhydride of Example 3, 10.7 g of octa-methylcyclotetrasiloxane and 50 ml of dry toluene. The resulting solution was refluxed for 2 hours. After cooling, carbon black was added and the solution was heated to 100° C. for 1 hour. Filtration and evaporation gave a colorless viscous oil. Based on method of preparation, the product was an anhydride terminated polydimethylsiloxane having the formula,

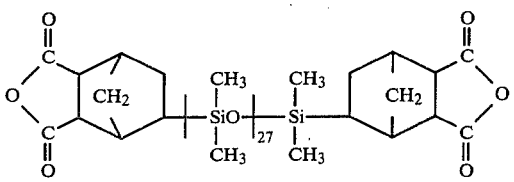

The identity of the product was further confirmed by NMR and IR analysis.

EXAMPLE 5

The solution of 6.57 g (0.04 mole) of 5-norbornene-2,3-dicarboxylic anhydride, 61.3 g of methylhydrogendimethylsiloxane copolymer having 3.4 wt% (H)CH₃SiO and a MW of 30,000, 100 ml of chlorobenzene and 10 drops of the Pt catalyst of Example 1 was heated to 80° C. overnight. After addition of carbon black, the mixture was stirred 1 hour at room temperature. Filtration and evaporation of low boiling materials under vacuum gave a colorless viscous residue. Based on method of preparation, the product was norbornane anhydride functionalized polysiloxane having the formula,

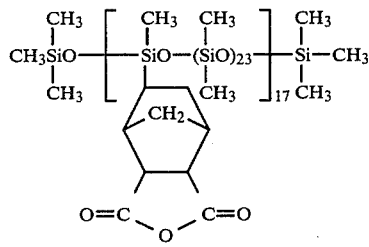

The identity of the produce was further confirmed by NMR and IR.

A blend of 10 parts of the above norbornane anhydride functionalized polysiloxane is blended as an adhesion promoter with 100 parts of a room temperature vulcanizable polydimethylsiloxane as shown by Beers et al, U.S. Pat. No. 3,541,044, assigned to the same assignee as the present invention.

EXAMPLE 6

The procedure of Example 1 was repeated, except there was used 0.02 mol of the 5-norbornene-2,3-dicarboxylic acid anhydride and 0.24 mol of the disiloxane. The resulting mixture was stirred at 60°–80° C. for 8 hours. Upon work-up there was obtained a colorless viscous oil in quantitative yield. Based on method of preparation, the product was

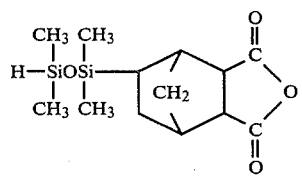

Its identity was confirmed by NMR and IR. The compound is found useful as an adhesive promoter for room temperature vulcanizable compositions.

Although the above examples are directed to only a few of the very many variables involved in the practice of the present invention, it should be understood that the present invention is directed to a much broader variety of silylnorbornanes which include the corresponding mono- and bis-anhydrides thereof as well as the disiloxanes and polysiloxane. These materials are made by hydrosilation of norbornene anhydride of formula (2) with silicon hydride of formula (3).

In addition to the mono and dianhydrides as shown by formula (2), there is also included within the scope of the present invention silyl polynorbornane anhydrides having the formula,

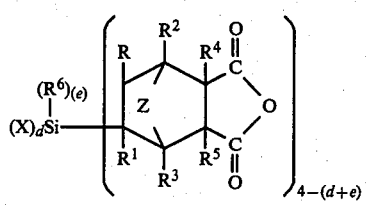

where R-R$^6$, X and Z are as previously defined, d is equal to 0 or 1, e is equal to 0 to 2 and the sum of d+e is equal to 1 or 2.

What I claim as new and desire to secure by Letters Patent of the United States is:

1. Silylnorbornane anhydrides of the formula

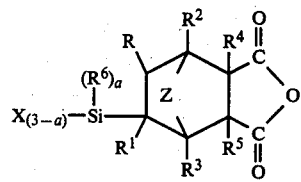

where R-R$^5$ are members selected from hydrogen, halogen, C$_{(1-13)}$ monovalent hydrocarbon radicals and substituted monovalent hydrocarbon radicals, Z is selected from —O— and C—(R)$_2$, R$^6$ is a member selected from monovalent hydrocarbon radicals and substituted monovalent hydrocarbon radicals, and X is a member selected from the class consisting of, (a) a hydrolyzable radical selected from the class consisting of halo, hydrogen, C$_{(1-8)}$ alkoxy, acyloxy, —N(R$^7$)$_2$, cyano, hydrogen, amido, carbamato, enoxy, imidato, isocyanato, oximato, isocyanate, oximato, thioisocyanato and ureido, (b) siloxanes having the formula,

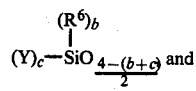

and (c) polysiloxanes having the formula,

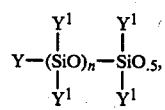

R$^7$ is selected from monovalent hydrocarbon radicals and Y is selected from a radical having the formula,

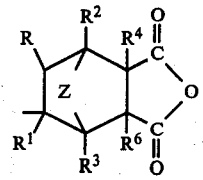

and (a) radicals, Y$^1$ is selected from R$^6$ radicals, Y radicals and mixtures thereof, a is a whole number equal to 0 to 3 inclusive, b is a whole number equal to 0 to 3 inclusive; c is a whole number equal to 0 to 3 inclusive, the sum of b+c is equal to 0 to 3 inclusive and n is an integer equal to 1 to 2000 inclusive.

2. Monoanhydrides of the formula,

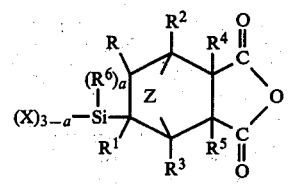

where R-R$^5$ are are a members selected from hydrogen, halogen, C$_{(1-13)}$ monovalent hydrocarbon radical and substituted C$_{(1-13)}$ monovalent hydrocarbon radicals, R$^6$ is a member selected from C$_{(6-13)}$ monovalent hydrocarbon radicals, and substituted C$_{(6-13)}$ monovalent hydrocarbon radicals, X is a hydrolyzable radical selected from halo, hydrogen, C$_{(1-8)}$ alkoxy, acyloxy, —N(R$^7$)$_2$, cyano, hydrogen, amido, carbamato, enoxy, imidato, isocyanato, oximato, isocyanate, oximato, thioisocyanato and ureido, R$^7$ is selected from monovalent hydrocarbon radicals Z is selected from —O—and C—(R)$_2$, and a is a whole number equal to 0 to 3 inclusive.

3. The compound

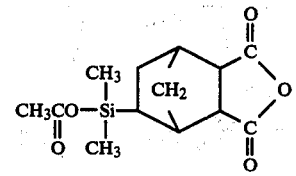

4. The compound

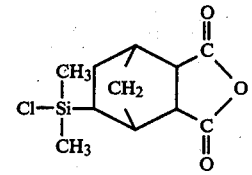

5. The compound

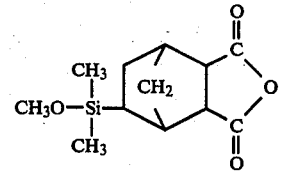

6. The compound

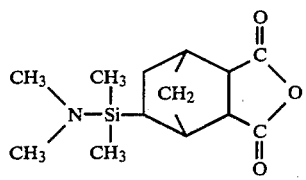

7. The compound

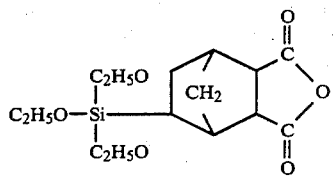

8. The compound

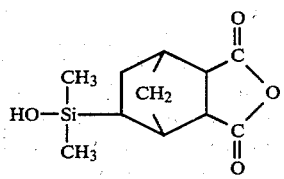

9. The compound

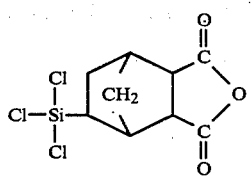

10. The compound

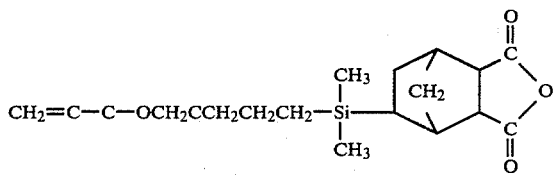

11. The compound

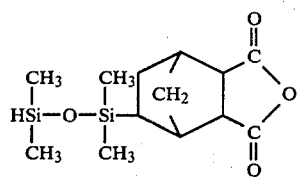

12. Dianhydrides of the formula,

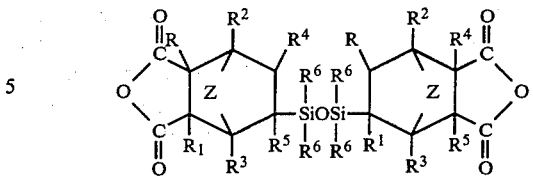

where R-$R^5$ is selected from hydrogen, halogen, $C_{(1-13)}$ monovalent hydrocarbon radical and substituted $C_{(1-13)}$ monovalent hydrocarbon radicals, $R^6$ is a member selected from $C_{(1-13)}$ monovalent hydrocarbon radicals and substituted $C_{(1-13)}$ monovalent hydrocarbon radicals and Z is selected from —O— and —C(R)$_2$—.

13. The compound

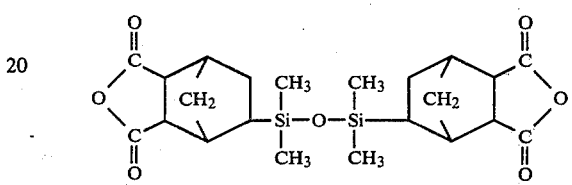

14. Dianhydride terminated polydiorganosiloxanes of the formula,

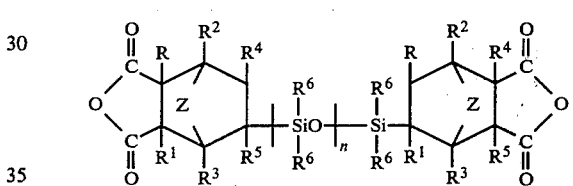

where R-$R^5$ are selected from hydrogen, halogen, $C_{(1-13)}$ monovalent hydrocarbon radicals and substituted $C_{(1-13)}$ monovalent hydrocarbon radicals, $R^6$ is selected from $C_{(1-13)}$ monovalent hydrocarbon radicals and substituted $C_{(1-13)}$ monovalent hydrocarbon radicals, Z is selected from —O— and —C(R)$_2$—, and n is an integer equal to 1 to 2000 inclusive.

15. Dianhydride terminated polydiorganosiloxane of the formula,

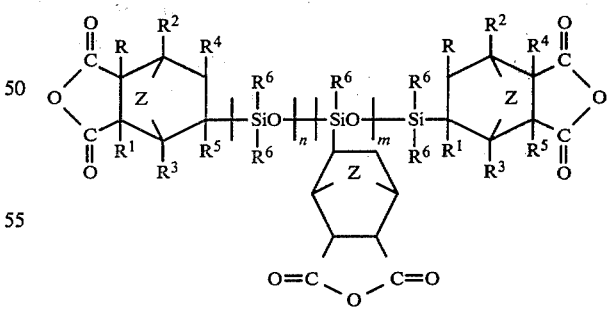

where R-$R^5$ are members selected from hydrogen and a $C_{(1-8)}$ alkyl radical, $R^6$ is selected from a $C_{(1-13)}$ monovalent hydrocarbon radical and substituted $C_{(1-13)}$ monovalent hydrocarbon, Z is selected from —O— and —C(R)$_2$—, n is an integer equal to 1 to 2000 inclusive, m is an integer equal to 0 to 100 inclusive and the sum of n+m is equal to 2 to 2000 inclusive.

16. Silyl polynorbornane anhydrides having the formula,

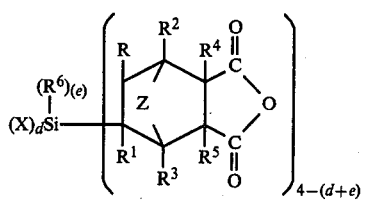

R-R⁵ are members selected from hydrogen and a $C_{(1-8)}$ alkyl radical, $R^6$ is selected from a $C_{(1-13)}$ monovalent hydrocarbon radical and substituted $C_{(1-13)}$ monovalent hydrocarbon, Z is selected from —O— and —C(R)₂—, X is a hydrolyzable radical selected from halo, hydrogen, $C_{(1-8)}$ alkoxy, acyloxy, —N(R⁷)₂, cyano, hydrogen, amido, carbamato, enoxy, imidato, isocyanato, oximato, isocyanate, oximato, and thioisocyanato, d is equal to 0 or 1, e is equal to 0 to 2 and the sum of d+e is equal to 1 or 2.

17. A method for making silylnorbornane anhydrides included within formula (1) which comprises effecting reaction between norbornene anhydride of the formula,

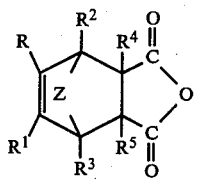

with a silane of the formula,

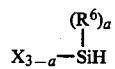

in the presence of an effective amount of a platinum catalyst, where X is a member selected from the class consisting of,
(a) a hydrolyzable radical selected from the class consisting of halo, hydrogen, $C_{(1-8)}$ alkoxy, acyloxy, —N(R⁶)₂, cyano, hydrogen, amido, amino, carbamato, enoxy, imidato, isocyanato, oximato, isocyanate, oximato, thioisocyanato and ureido,
(b) siloxanes having the formula,

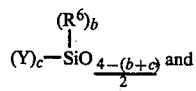

(c) polysiloxanes having the formula,

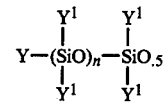

where R-R⁵ are members selected from hydrogen and $C_{(1-8)}$ alkyl, $R^6$ is selected from a $C_{(1-13)}$ monovalent hydrocarbon radical and substituted $C_{(1-13)}$ monovalent hydrocarbon, Y is selected from a radical having the formula,

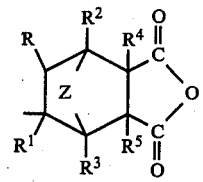

and (a) radicals, $Y^1$ is selected from $R^6$ radicals, Y radicals and mixtures thereof, Z is selected from —O— and C—(R)₂, a is a whole number equal to 0 to 3 inclusive, b is a whole number equal to 0 to 3 inclusive, c is a whole number equal to 0 to 3 inclusive, the sum of b+c is equal to 0 to 3 inclusive, and n is an integer equal to 1 to 2000 inclusive.

18. A method for making dianhydride terminated polydiorganosiloxane which comprises equilibrating an anhydride terminated diorganosiloxane of the formula,

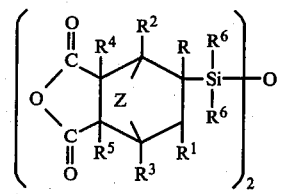

with a cyclopolydiorganosiloxane of the formula,

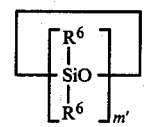

in the presence of an acid catalyst, where where R-R⁵ are members selected from hydrogen and $C_{(1-8)}$ alkyl, $R^6$ is selected from a $C_{(1-13)}$ monovalent hydrocarbon radical and substituted $C_{(1-13)}$ monovalent hydrocarbon, Z is selected from —O— and C—(R)₂, and m' has a value of 3 to 6 inclusive.

* * * * *

UNITED STATES PATENT AND TRADEMARK OFFICE
CERTIFICATE OF CORRECTION

PATENT NO. : 4,381,396

DATED : April 26, 1983

INVENTOR(S) : Hong-Son Ryang

It is certified that error appears in the above-identified patent and that said Letters Patent is hereby corrected as shown below:

Column 11, line 53, cancel

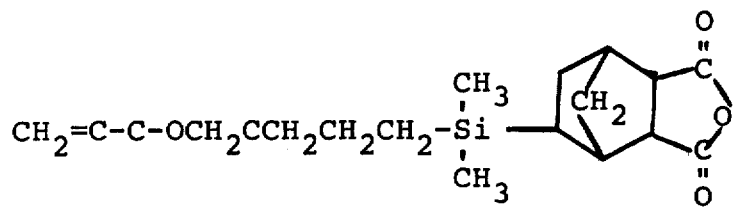

and substitute

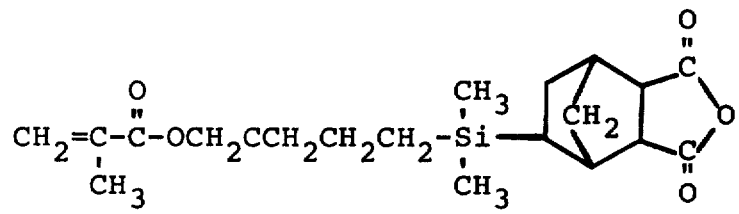

Signed and Sealed this

Nineteenth Day of July 1983

[SEAL]

Attest:

Attesting Officer

GERALD J. MOSSINGHOFF

Commissioner of Patents and Trademarks